US009958428B2

(12) United States Patent
Hamby

(10) Patent No.: US 9,958,428 B2
(45) Date of Patent: May 1, 2018

(54) SCANNING SYSTEM FOR WOOD

(71) Applicant: HASKAN, LLC, Soddy Daisy, TN (US)

(72) Inventor: W. Daniel Hamby, Valdese, NC (US)

(73) Assignee: HASKAN, LLC, Soddy Daisy, TN (US)

( * ) Notice: Subject to any disclaimer, the term of this patent is extended or adjusted under 35 U.S.C. 154(b) by 203 days.

(21) Appl. No.: 14/879,823

(22) Filed: Oct. 9, 2015

(65) Prior Publication Data
US 2016/0103115 A1   Apr. 14, 2016

Related U.S. Application Data

(60) Provisional application No. 62/061,826, filed on Oct. 9, 2014.

(51) Int. Cl.
G01N 29/04 (2006.01)
G01N 21/00 (2006.01)
G01N 33/46 (2006.01)
G01N 21/95 (2006.01)
G01N 29/22 (2006.01)

(52) U.S. Cl.
CPC ............ G01N 33/46 (2013.01); G01N 21/95 (2013.01); G01N 29/043 (2013.01); G01N 29/225 (2013.01); G01N 2291/0238 (2013.01); G01N 2291/102 (2013.01); G01N 2291/104 (2013.01); G01N 2291/2698 (2013.01)

(58) Field of Classification Search
CPC ...... G01N 33/46; G01N 21/95; G01N 29/043; G01N 29/225
See application file for complete search history.

(56) References Cited

U.S. PATENT DOCUMENTS

| 3,825,046 A * | 7/1974 | Peterson | B27C 5/02 144/117.3 |
| 3,942,021 A | 3/1976 | Barr et al. | |
| 4,149,089 A | 4/1979 | Idelsohn et al. | |
| 4,286,880 A | 9/1981 | Young | |
| 5,097,881 A * | 3/1992 | Mack | B07C 5/14 144/24.13 |
| 5,412,220 A | 5/1995 | Moore | |
| 5,703,960 A | 12/1997 | Soest | |
| 5,761,070 A * | 6/1998 | Conners | B07C 5/3422 345/426 |
| 5,892,808 A * | 4/1999 | Goulding | G01N 23/046 378/58 |
| 5,960,104 A * | 9/1999 | Conners | G01N 21/8986 144/402 |
| 6,122,065 A * | 9/2000 | Gauthier | G01N 21/8986 356/391 |
| 6,241,073 B1 * | 6/2001 | McAllister | B27N 3/143 198/382 |
| 6,366,351 B1 * | 4/2002 | Ethier | G01N 21/8986 356/237.1 |

(Continued)

Primary Examiner — Helen Kwok
(74) Attorney, Agent, or Firm — Jeffrey C. Watson; Mathew L. Grell; Grell & Watson Patent Attorneys LLC

(57) ABSTRACT

A scanning system to analyze wood and determine defects includes at least two ultrasonic transducers configured to scan the wood from edge to edge by triangulating the wood. The at least two ultrasonic transducers are configured to find splits and shakes.

13 Claims, 8 Drawing Sheets

(56) References Cited

U.S. PATENT DOCUMENTS

| | | | |
|---|---|---|---|
| 6,367,330 B1* | 4/2002 | Schafer | G01N 29/30 73/597 |
| 6,457,363 B1* | 10/2002 | Schafer | G01N 29/2493 73/596 |
| 7,356,175 B2 | 4/2008 | Lee et al. | |
| 7,429,999 B2* | 9/2008 | Poulin | G06T 7/521 348/187 |
| 8,502,180 B2* | 8/2013 | Bouchard | G01N 21/8901 250/223 R |
| 2003/0042180 A1* | 3/2003 | Kairi | B07C 5/14 209/518 |
| 2003/0192412 A1* | 10/2003 | Otto | B07C 5/14 83/13 |
| 2005/0161118 A1* | 7/2005 | Carman | B07C 5/14 144/403 |
| 2006/0259252 A1* | 11/2006 | Leitinger | B27G 1/00 702/43 |
| 2007/0267104 A1* | 11/2007 | McGehee | B27C 1/12 144/373 |
| 2008/0099105 A1 | 5/2008 | Kelly | |
| 2008/0197054 A1* | 8/2008 | Lindstrom | G01B 17/06 209/517 |
| 2008/0236704 A1* | 10/2008 | Risi | B23D 59/001 144/356 |
| 2011/0002527 A1 | 1/2011 | Jeong et al. | |
| 2016/0346851 A1* | 12/2016 | Maki-Haapoja | B23D 59/001 |
| 2016/0375718 A1* | 12/2016 | Van Garsse | B44C 5/04 52/311.1 |
| 2017/0024925 A1* | 1/2017 | Palmer | G06T 15/04 |

* cited by examiner

SCANNING SYSTEM FOR WOOD

CROSS REFERENCE TO RELATED APPLICATIONS

To the full extent permitted by law, the present U.S. Non-provisional Patent Application hereby claims priority to and the full benefit of U.S. Provisional Application entitled "Scanning System for Hardwood Flooring," having assigned Ser. No. 62/061,826, filed on Oct. 9, 2014, incorporated herein by reference in its entirety.

FEDERALLY SPONSORED RESEARCH OR DEVELOPMENT

None

PARTIES TO A JOINT RESEARCH AGREEMENT

None

REFERENCE TO A SEQUENCE LISTING

None

BACKGROUND OF THE DISCLOSURE

Technical Field of the Disclosure

The present disclosure generally relates to wood, lumber or boards, like hardwood flooring, and devices and methods of scanning thereof.

Description of the Related Art

Wood, as used herein, may refer to any wood, lumber, or boards that may be cut, processed, etc. to become the finished product, like hardwood flooring. As such, in order to make sure that the wood is free of defects, the wood needs to be scanned. Board scanners, like hardwood flooring scanners, or hardwood flooring scanning systems, are known and currently used by some hardwood flooring manufacturers and suppliers. However, to date, the scanners or systems that are currently being used are limited to visual defects and can not find underlying splits and shakes. In addition, the scanning systems currently used are not very accurate.

Therefore, it is readily apparent that there is a recognizable unmet need for a scanning system for wood, like hardwood flooring, that is more accurate than known systems and can find underlying splits and shakes. The instant disclosure of a scanning system for wood is designed to address at least one or more of the above mentioned problems.

SUMMARY

Briefly described, in a preferred embodiment, the present scanning system for wood, like hardwood flooring wood, lumber or board, overcomes the above-mentioned disadvantages and meets the recognized need for such a system adapted to analyze wood and determine defects. The instant disclosure of a scanning system may be for scanning and analyzing wood for finding defects therein. Although the disclosure is clearly not limited thereto and may be used for scanning any wood, lumber or boards, the instant disclosure may be used to scan hardwood flooring for defects therein.

One feature of the instant scanning system may be the inclusion of at least two ultrasonic transducers adapted to scan the wood from edge to edge. The ultrasonic transducers may be adapted to triangulate for scanning the wood from edge to edge. The ultrasonic transducers may also be adapted to give the best edge of the wood, like hardwood flooring. These ultrasonic transducers may confirm a hole by making sure of a true open area, whereby they may find splits and shakes that cameras can not find.

Another feature of the instant scanning system may be that the ultrasonic transducers may be set to an optimum frequency for scanning wood, like hardwood flooring. In one embodiment, the frequency may be between 60-80 khz. In another embodiment, the frequency may be between 120-124 khz. In a possibly preferred embodiment, the frequency may be 124 khz.

Another feature of the instant scanning system may be that the ultrasonic transducers may include a pulsar (sender) and a receiver. The pulsar (sender) and the corresponding receiver may be oriented at the same angle relative to the side of the wood. In one embodiment, the angle may be between 5 degrees and 20 degrees. In another embodiment, the angle may be between 7 degrees and 18 degrees. In a possibly preferred embodiment, the angle may be between 10 degrees and 15 degrees.

Another feature of the instant scanning system may be that the two ultrasonic transducers may have an air gap between the sensors and the wood. In one embodiment, the air gap may be between 0.1 inches and 1 inch. In another embodiment, the air gap may be between 0.25 inches and 0.75 inches. In a possibly preferred embodiment, the air gap may be approximately ½ inch.

Another feature of the instant scanning system may be that the air gap can be maintained by providing the pulsar (sender) and/or the receiver on a floating head. In one embodiment, the floating head may have an angled front.

Another feature of the instant scanning system may be that the receivers may be offset in the direction of the face angle a distance equal to the width of the transducer. In this embodiment, the offset alignment may allow each transducer's sonic cone to align parallel with its adjacent pair. This offset may provide for optimum triangulation of the wood by the ultrasonic transducers.

Another feature of the instant scanning system may be the inclusion of at least one camera for visual defects. The camera or cameras may be for imaging the top and bottom surface of the wood. In select embodiments, the cameras may include a monochrome camera, a true color area scan camera, and/or a 3D profiling camera.

Another feature of the instant scanning system may be that the camera or cameras may include structured lighting. In select embodiments, the structured lighting may include: invisible infrared ("night vision") lighting for the monochrome camera adapted to image rough sawn wood samples, reduce the contrast of color variance, and/or aid in the analysis of defects for rough side processing; natural white lighting for the true color cameras adapted to enhance contrast, and/or to aid in the analysis of defects and wood grade for surfaced/milled wood samples; and/or invisible or visible lasers with line generators for the 3D profiling camera adapted to strike the surface of the sample at 45° being offset respective of the surface's irregularity.

Another feature may be that the camera or cameras can be adapted to decontrast the wood.

Another feature of the instant scanning system may be that the ultrasonic transducers and the camera or cameras may combine to analyze the wood, like hardwood flooring, and determine defects.

Another feature of the instant scanning system may be the inclusion of a feed conveyor with a cradle adapted to bring the wood in on two sides. This feature may allow the wood, lumber or boards, like hardwood flooring to bow naturally.

Another feature of the instant scanning system may be that it can include a feed conveyor, a scan box, a tail conveyor, or combinations thereof. In select embodiments, the instant scanning system may include the feed conveyor, the scan box, and the tail conveyor.

Another feature of the instant scanning system may be the inclusion of a programmable logic controller (PLC), computer, computer system, the like, or combination thereof adapted to control the feed conveyor, the scan box, the tail conveyor, or combinations thereof.

Another feature of the instant scanning system may be the ability to have two different setups, a first setup for rough, and a second setup for surfaced (milled).

The instant disclosure also includes a method of scanning wood utilizing the scanning system according to any of the embodiments shown, described, or claimed herein.

These and other features of the scanning system for wood will become more apparent to one skilled in the art from the prior Summary, and following Brief Description of the Drawings, Detailed Description, and Claims when read in light of the accompanying Detailed Drawings.

BRIEF DESCRIPTION OF THE DRAWINGS

The present scanning system for wood, like hardwood flooring, will be better understood by reading the Detailed Description with reference to the accompanying drawings, which are not necessarily drawn to scale, and in which like reference numerals denote similar structure and refer to like elements throughout, and in which.

It is to be noted that the drawings presented are intended solely for the purpose of illustration and that they are, therefore, neither desired nor intended to limit the disclosure to any or all of the exact details of construction shown, except insofar as they may be deemed essential to the claimed invention.

DETAILED DESCRIPTION

In describing the exemplary embodiments of the present disclosure, as illustrated in FIGS. 1-8, specific terminology is employed for the sake of clarity. The present disclosure, however, is not intended to be limited to the specific terminology so selected, and it is to be understood that each specific element includes all technical equivalents that operate in a similar manner to accomplish similar functions. Embodiments of the claims may, however, be embodied in many different forms and should not be construed to be limited to the embodiments set forth herein. The examples set forth herein are non-limiting examples, and are merely examples among other possible examples.

Scanning system 10 may be used for scanning any wood 12 or like materials for defects. Wood 12, as used herein, may refer to any wood, lumber or boards, like hardwood flooring wood. Scanning system 10 may be ideally suited for scanning hardwood flooring wood 12 for defects, but the invention is not so limited, and scanning system 10 may be used for any wood, lumber, boards, like materials, or combinations thereof.

Figure 1:
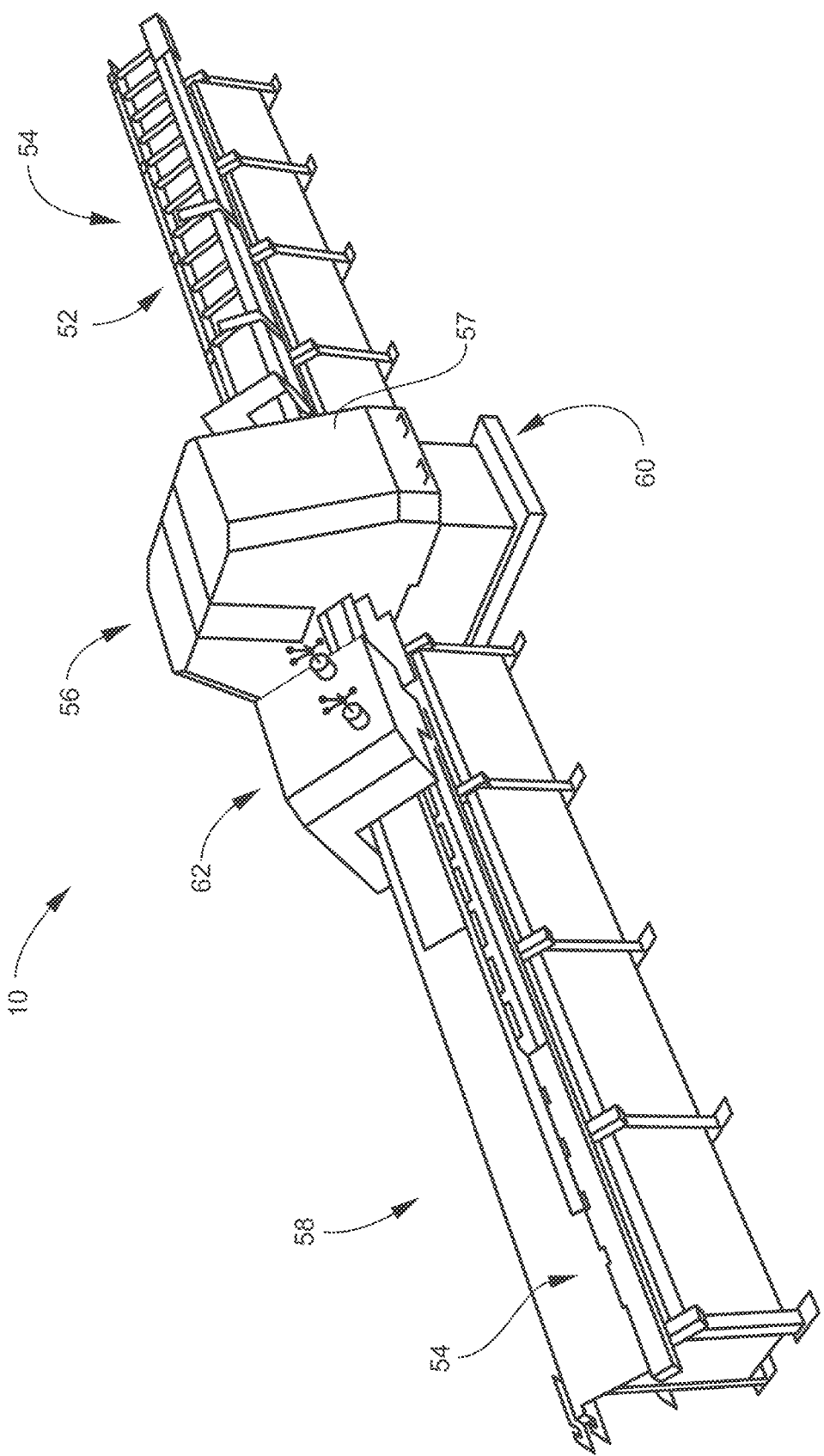
FIG. 1 is a perspective view of an exemplary embodiment of the scanning system for wood according to the instant disclosure.

Referring now to FIG. 1 by way of example, and not limitation, therein is illustrated an example embodiment scanning system 10 for wood, wherein scanning system 10 may generally include feed conveyor 52, scan box 56, and tail conveyor 58. Computer device 60 may be included with scanning system 10, like in scan box 56. Pinch roll assembly 62 may be included with scanning system 10 on or before tail conveyor 58. These parts are described in detail below.

Figure 2:
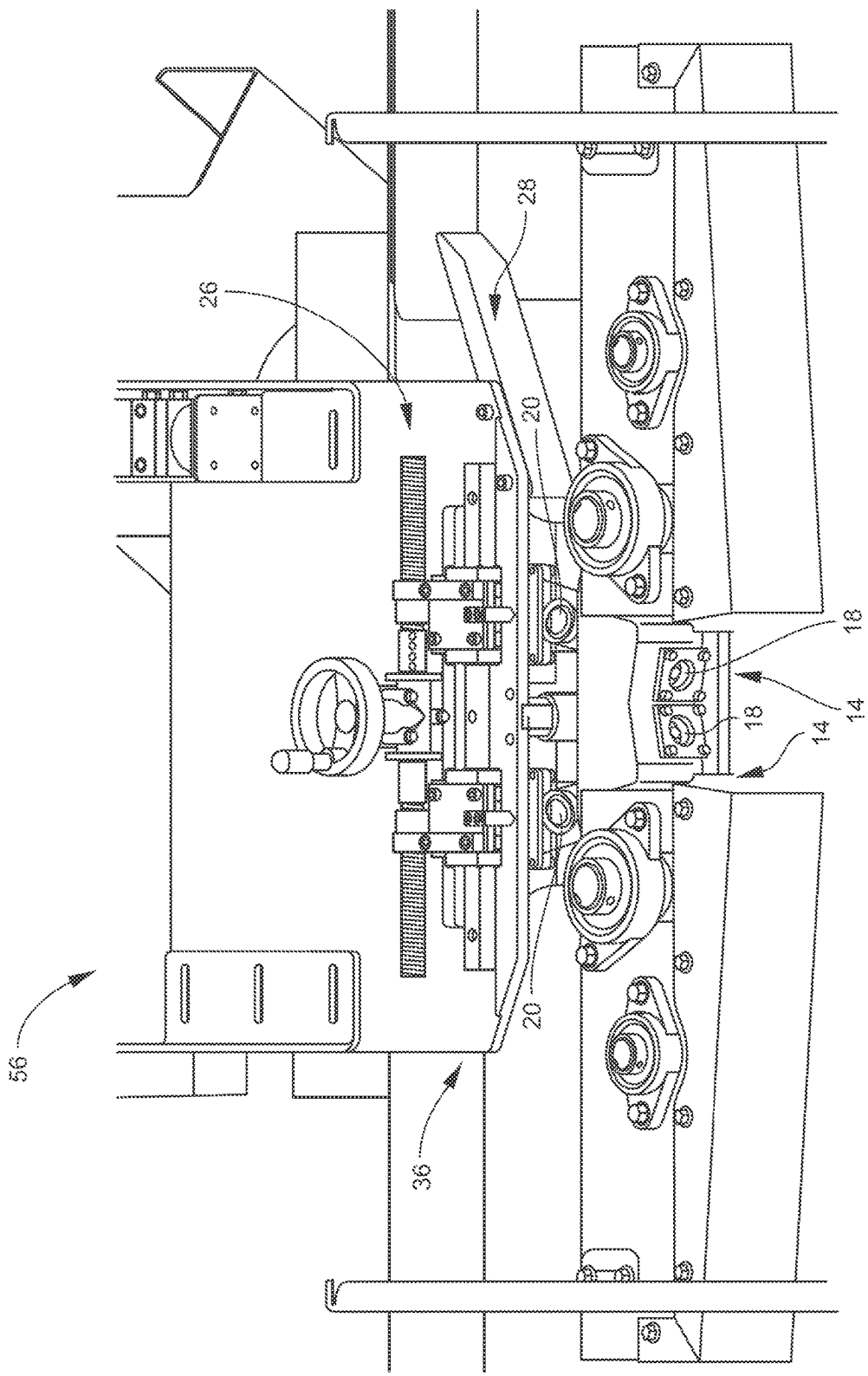
FIG. 2 is a perspective view of the scan box from FIG. 1 with the cover removed.
Figure 3:
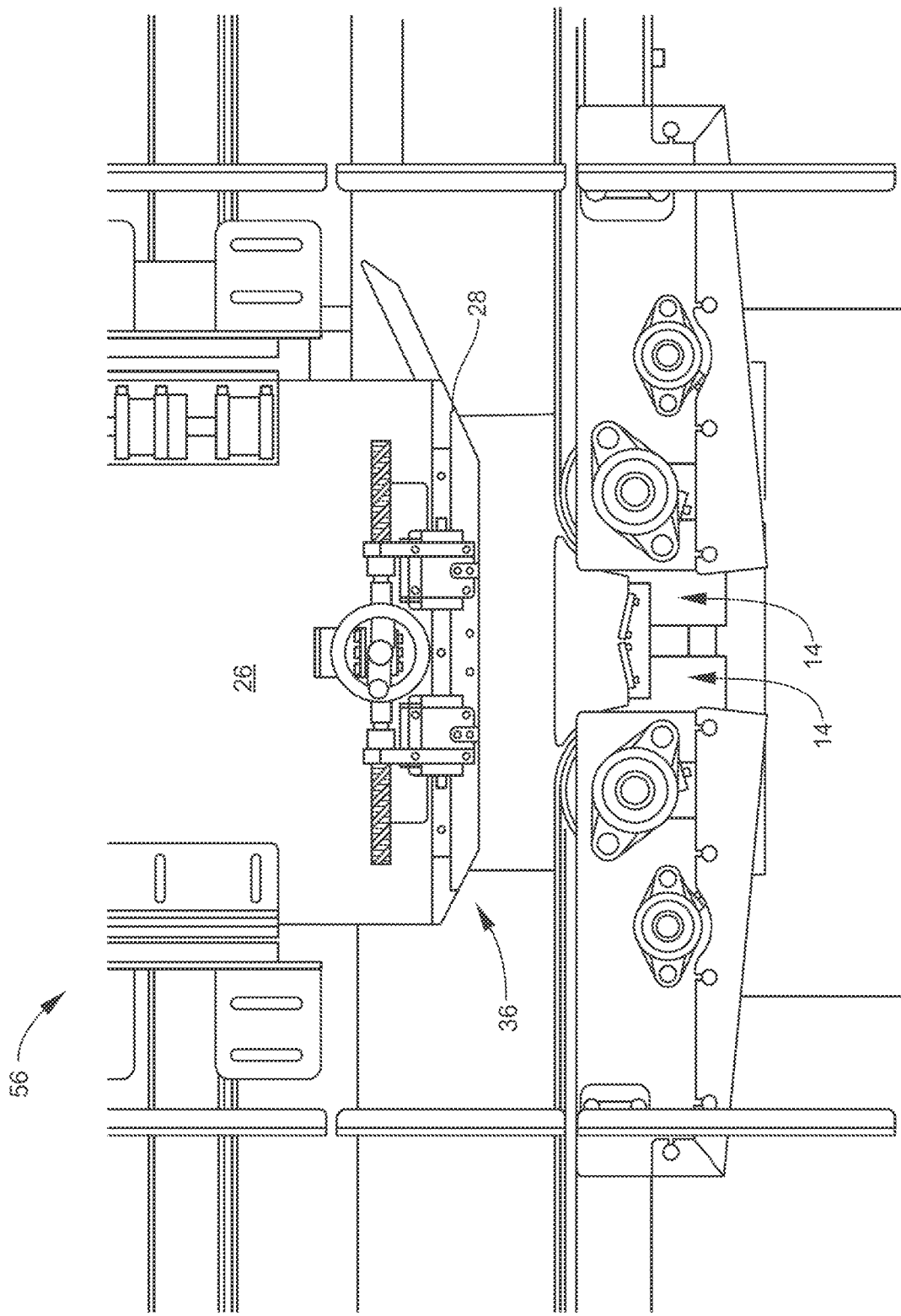
FIG. 3 is a side view of the scan box from FIG. 1 with the cover removed.

Scan box 56 may be the area where scanning system 10 may scan wood 12. Scan box 56 may include a cover 57 or removable enclosure for accessing scan box 56. Referring now to FIGS. 2-3, scan box 56 is shown with cover 57 removed showing the inner structures and mechanisms of scan box 56. One feature of scan box 56 may be the at least two ultrasonic transducers 14. Ultrasonic transducers 14 may be for detecting underlying defects, including, but not limited to, splits, shakes, the like, etc. Ultrasonic transducers 14 may be configured to scan wood 12 from edge to edge. Ultrasonic transducers 14 may also be configured to triangulate for scanning wood 12 from edge to edge. Ultrasonic transducers 14 may also be configured to give the best edge of wood 12. These ultrasonic transducers 14 may confirm a hole by making sure of a true open area, whereby they may find splits and shakes that cameras can not find. Ultrasonic transducers 14 may be set to an optimum frequency for scanning wood 12. In one embodiment, the frequency may be between 60-80 khz. In another embodiment, the frequency may be between 120-124 khz. In a possibly preferred embodiment, like for hardwood flooring board 12, the frequency may be 124 khz.

Figure 4:
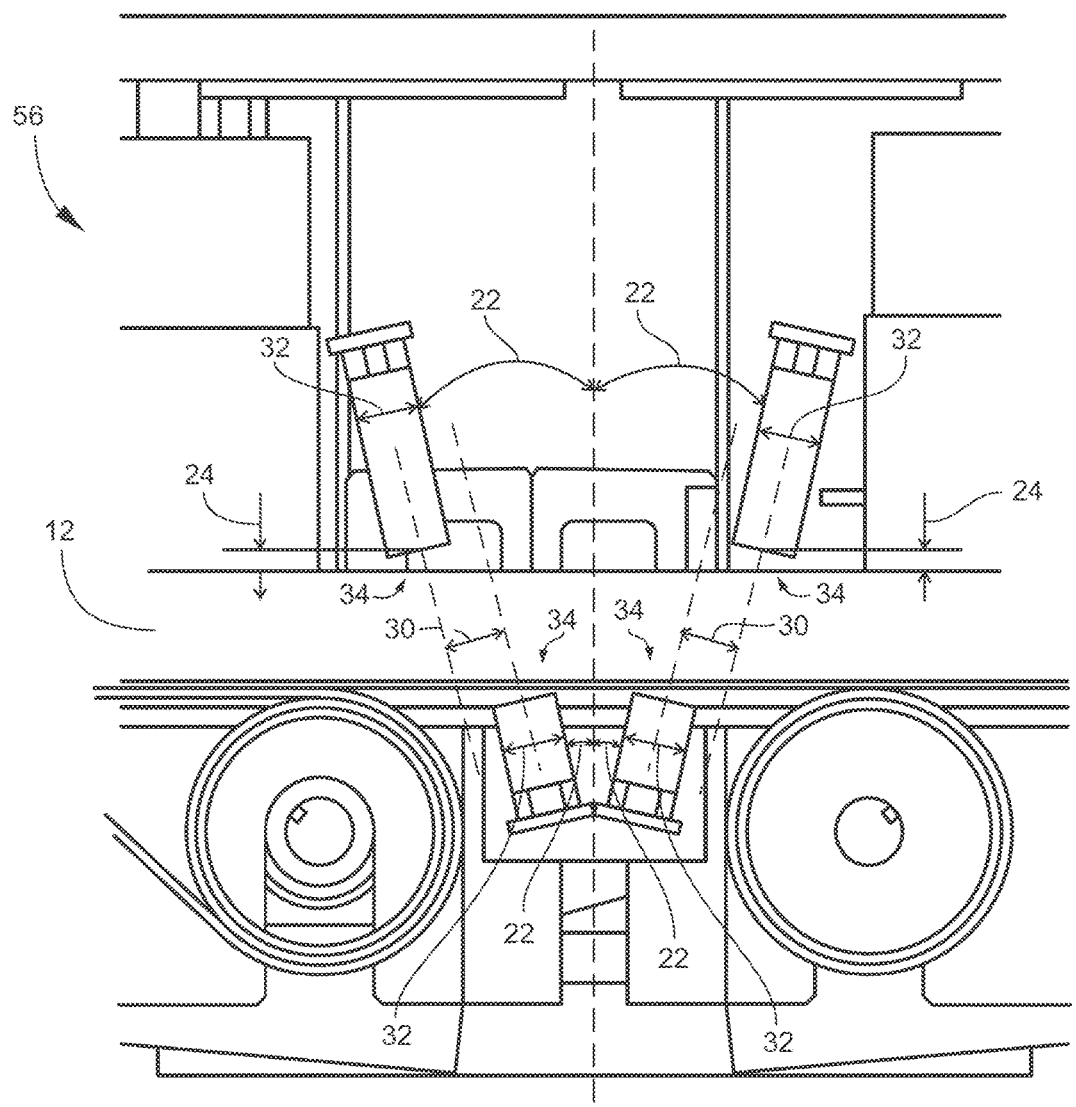
FIG. 4 is a partially cut away side view of an exemplary embodiment of the scan box according to the instant disclosure showing the ultrasonic transducers.

Referring now to FIG. 4, another feature of scanning system 10 may be that each ultrasonic transducer 14 may include pulsar (sender) 18 and receiver 20. Pulsar 18, or the sender, and the corresponding receiver 20 may be oriented at angle 22 relative to the side of wood 12. Angle 22 may be the same for pulsar 18 and its corresponding receiver 20. In one embodiment, angle 22 may be between 5 degrees and 20 degrees. In another embodiment, angle 22 may be between 7 degrees and 18 degrees. In a possibly preferred embodiment, like for hardwood flooring board 12, angle 22 may be between 10 degrees and 15 degrees.

Referring still to FIG. 4, another feature of scanning system 10 may be that each ultrasonic transducers 14 may have air gap 24 between each sensor and wood 12. In one embodiment, air gap 24 may be between 0.1 inches and 1 inch. In another embodiment, air gap 24 may be between 0.25 inches and 0.75 inches. In a possibly preferred embodiment, like for hardwood flooring board 12, air gap 24 may be approximately 0.50 inches.

Referring now back to FIGS. 2 and 3, another feature of scanning system 10 may be that air gap 24 can be maintained by providing pulsar 18 and/or receiver 20 on floating head 26. Floating head 26 may be configured to move freely up and down depending on the thickness of board 12 in order to maintain air gap 24. Angled front 28 may be included at the front end of floating head 26 for contacting board 12 allowing board 12 to move floating head 26 up and/or down in order to maintain air gap 24.

Referring now back to FIG. 4, another feature of scanning system 10 may be that each receiver 20 may be offset distance 30 in the direction of angle 22. This offset distance 30 may be equal to width 32 of transducer 14. In this embodiment, the offset alignment may allow each transducer's sonic cone 34 to align parallel with its adjacent pair. This offset of sonic cones 34 may provide for optimum triangulation of the wood by the ultrasonic transducers 14.

Figure 5:
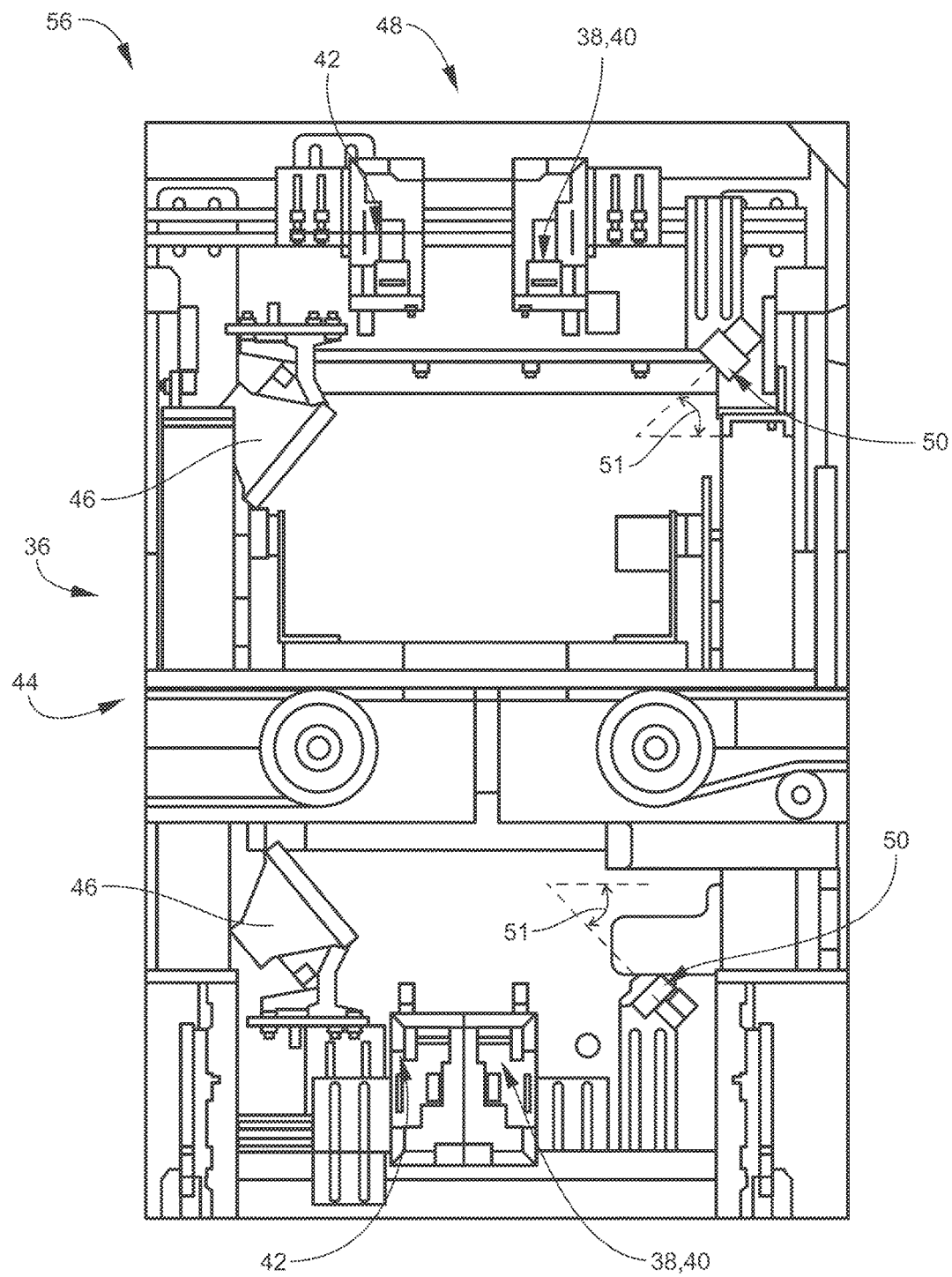
FIG. 5 is a partially cut away side view of an exemplary embodiment of the scan box according to the instant disclosure showing the cameras and structured lighting.

Referring now to FIG. 5, another feature of scanning system 10 may be the inclusion of at least one camera 36 in scan box 56. The cameras 36 may be for detecting visual defects. The camera or cameras 36 may be for imaging the top and bottom surface of wood 12. In select embodiments, cameras 36 may include monochrome camera 38, true color area scan camera 40, and/or 3D profiling camera 42. Structured lighting 44 may be included for illuminating board 12 for cameras 36. Structured lighting 44 may include, but is not limited to: invisible infrared ("night vision") lighting 46 for monochrome camera 38 configured to image rough sawn wood samples, reduce the contrast of color variance, and/or aid in the analysis of defects for rough side processing; natural white lighting 48 for the true color cameras 40 configured to enhance contrast, and/or to aid in the analysis of defects and wood grade for surfaced/milled wood samples; and/or invisible or visible lasers 50 with line generators for the 3D profiling camera configured to strike the surface of the sample at angle 51. In select embodiments, angle 51 may be 45°, or approximate thereto, being offset respective of the surface's irregularity. Camera or cameras 36 can be configured to decontrast wood 12. In combination with ultrasonic transducers 14, camera or cameras 36 may analyze wood 12, like hardwood flooring, and determine defects.

Referring back to FIG. 1, computer device 60 may be included with scanning system 10. Computer device 60 may be internal to scanning system 10, like in scan box 56 as shown, or it may be external or remotely connected to scanning system 10. Computer device 60 may control the functions of scanning system 10, including scan box 56, feed conveyor 52, tail conveyor 58, or any combinations thereof. Computer device 60 may be any computer or like device capable of controlling scanning system 10. For example, computer device 60 may be programmable logic controller (PLC), computer, computer system, the like, or combination thereof configured to control the feed conveyor, the scan box, the tail conveyor, or combinations thereof. In select embodiments, computer device 60 may be configured with two different setups, a first setup for rough, and a second setup for surfaced (milled). Computing device 60 or PLC may acquire all data and process, transmit, and display it.

Figure 6:
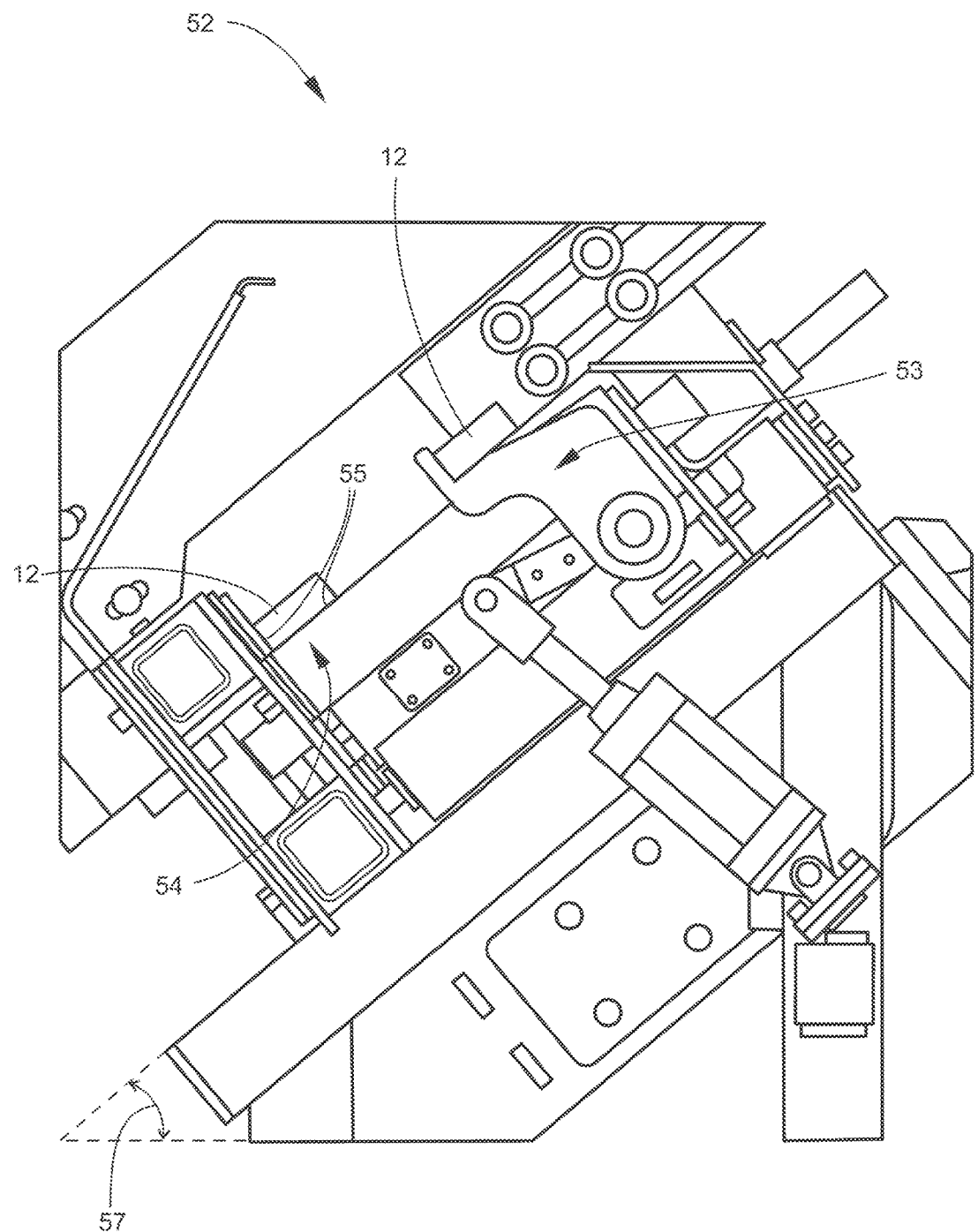
FIG. 6 is a side end view of an exemplary embodiment of the feed conveyor according to the instant disclosure.

Referring now to FIGS. 1 and 6, feed conveyor 52 is shown for scanning system 10. Feed conveyor 52 may be for bringing wood 12 into scan box 56. Feed conveyor 52 may include any device or means for moving wood 12 into scan box 56. One feature of feed conveyor 52 is cradle 54. Cradle 54 may be configured to bring wood 12 in on two sides 55. This feature of cradle 54 may allow wood 12, like hardwood flooring, to bow naturally as it is scanned by scanning system 10. As shown in the figures, feed conveyor 52 may be constructed with steel tubing, angle plate, and flat plate. The design may utilize a flat belt and un-powered rollers set at angle 57 (40° or approximate thereto) off horizontal mounted in the framework; and, a narrow rough top edge belt set normal or 90° to the flat belt. Together these two conveying belts may cradle wood 12 in a V-shape that may register the samples on two sides 55, bottom and edge. The cradling may control and stabilize the wood samples as it conveys through the system. Built into the conveyor and interfaced into the un-powered rollers may be multiple receiving arms 53 that may be interconnected together and may be raised and lowered by an air cylinder controlled by the system's computer device 60 or PLC.

Figure 7:
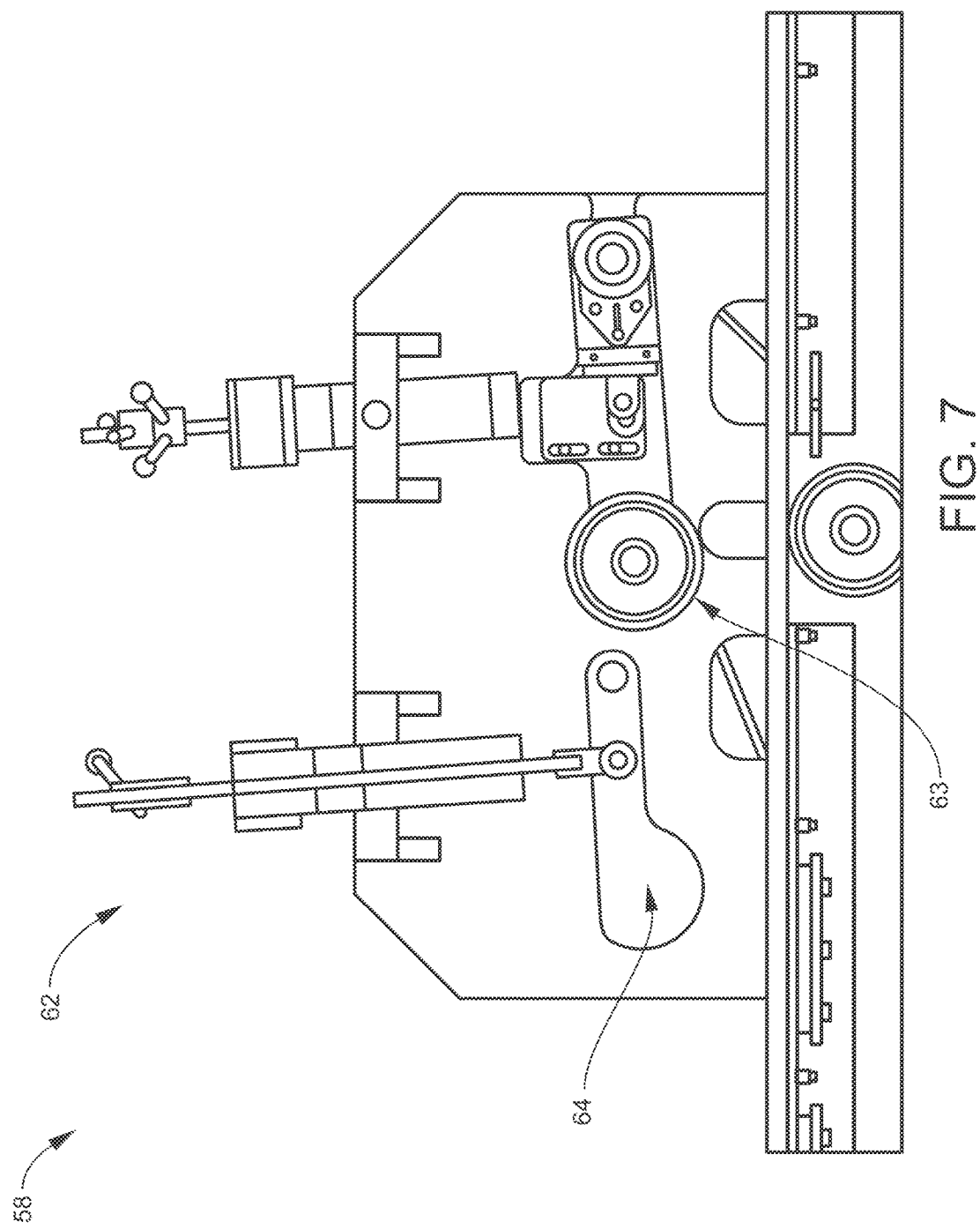
FIG. 7 is a side view of an exemplary embodiment of the pinch roll assembly of the tail conveyor according to the instant disclosure.
Figure 8:
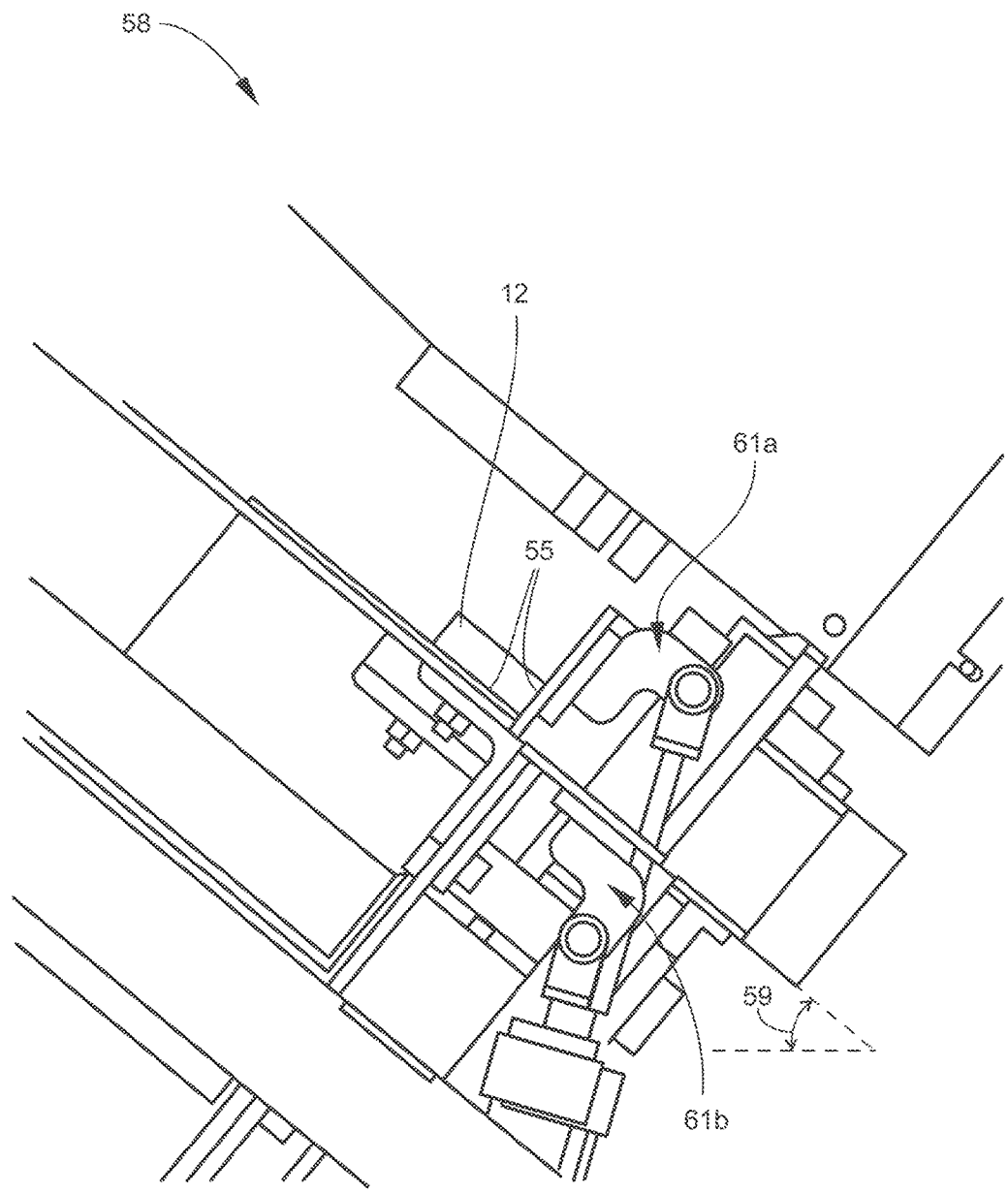
FIG. 8 is a side end view of an exemplary embodiment of the tail conveyor according to the instant disclosure showing the gate in the up position and the down position.

Referring to FIGS. 1 and 7-8, tail conveyor 58 is shown for scanning system 10. Tail conveyor 58 may be for removing wood 12 from scan box 56. Tail conveyor 58 may include any device or means for removing wood 12 from scan box 56. One feature of tail conveyor 58 is that it can include cradle 54, similar to feed conveyor 52. Cradle 54 may be configured to bring wood 12 out of scan box 56 on two sides 55. This feature of cradle 54 may allow wood 12, like hardwood flooring, to bow naturally as it is scanned by scanning system 10. As shown in the figures, tail conveyor 58 may be constructed with steel tubing, angle, and flat plate. The design may utilize a flat conveying belt that may be set at 40° off horizontal mounted in the framework; and, a narrow rough top edge belt set normal or 90° to the flat belt. Together these two conveying belts may cradle the wood samples in a V-shape that registers the samples on two sides 55, bottom and edge. A variety of designs may be envisioned where the length of both belts may vary with respect to how and where the wood sample may be transferred.

Referring specifically to FIG. 7, another feature of tail conveyor 58 may be the inclusion of pinch roll assembly 62 on or before tail conveyor 58. Pinch roll assembly 62 may control the movement of wood 12 from scan box 56. Pinch roll assembly may generally include pinch roll 63 and dead stop 64, which may operate in conjunction to move and stop board 12 quickly as it moves out of scan box 56. In select embodiments, short belts may be utilized for both flat and edge which may interface into the powered pinch roll 63 and dead stop 64, or the stopping brake system. Pinch roll 63 and dead stop 64 may be raised and lowered by an air cylinder, or separate air cylinders, controlled by the system's computer device 60 or PLC. Each air cylinder may have a separate pressure regulator to adjust clamping pressure.

Referring now to FIG. 8, incorporated into tail conveyor 58 may be a flat metal slide section and an edge fence that may receive wood 12 from the brake system 62. The slide may be set parallel with the flat belt. The edge fence 61 may be set normal or 90° to the slide and may be opened 61a and closed 61b by an air cylinder controlled by the system's computer device 60 or PLC.

In select embodiments, the feed conveyor 52 and tail conveyor 58 may be commonly powered. Attachment plates may interconnect, position, and align the feed and tail conveyors together. An encoder may be commonly driven by the conveying system drive. The conveyors may interconnect through scan box 56 and may provide conveyance of wood samples through scan box 56.

In an example embodiment, scan box 56 may be constructed with steel tubing, channel, and flat plates. The design may incorporate all mounting hardware for a series of sensors which may include cameras 36 and ultrasonic transducers 14. Fiberglass cover 57, or a plurality of covers 57, may be hinged on the framework. These covers 57 may open and close to provide access to the scan area of scan box 56. Mounted in the scan box 56 may be a pair of monochrome cameras 38 and/or true color area scan cameras 40 that may independently image the top and bottom surface of the samples 12. Special structured lighting 44 may be utilized for these cameras 36 with respect to its type. Invisible inferred "night vision" light 50 may be used for the monochrome cameras 38 that image rough sawn wood samples. This lighting may reduce the contrast of color variance and may aid in the analysis of defects for rough side processing. Natural white light may be used for the true color cameras to enhance contrast to aid in the analysis of defects and wood grade for surfaced/milled wood samples. Also mounted in scan box 56 may be a pair of 3D profiling cameras 42 that may image the top and bottom surfaces. These cameras 42 may be illuminated by invisible or visible lasers 50 with line generators that strike the surface of the sample at 45° being offset respective of the surface's irregularity. Multiple ultrasonic transducers 14 may be arrayed in scan box 56 to image the samples from edge to edge and/or top to bottom. Two pulser transducers 18 may inject sound into the sample on one side while two receiving transducers 20 on the other side may record all escaping sound. The alignment of these transducers may be critical to proper operation. For example, for hardwood flooring the face of each transducer 14 may be set at 10°-15° relative to the side of the sample and at a distance of approximately inch. The receivers 20 may be offset in the direction of the face angle offset distance 30 equal to the width 32 of transducer 14. This offset alignment may allow each transducer's sonic cone 34 to align parallel with its adjacent pair. The receivers 20 may be mounted in an assembly on floating head 26 that may be allowed to float next to the sample thereby maintaining a fixed distance (air gap 24) from the face of the sensor to the side of the sample.

In operation, a variety of material handling systems can/will deliver wood samples 12 to the feed conveyor 52 one piece at a time. Each sample 12 may be loaded onto the receiving arms 53 which hold the wood samples 12 up off of the conveyor belt/rollers. When the edge belt is clear and ready for a sample the arms 53 may drop releasing the wood sample 12 to slide down against the edge belt and onto the flat belt and into the conveying cradle 54 on two sides 55. The sample 12 may be transferred through scan box 56 moving over the gap between the feed and tail conveyors (see FIGS. 2-3). As the sample 12 moves a photoelectric sensor may tell the computer that a sample is ready to process. The two pairs of cameras 36 and the ultrasonic transducers 14 may record their individual data sets. All three data sets (area scan, 3D profile, and Ultrasonic) may be analyzed by proprietary software to determine all areas of interest or defects. The software may provide its user a work sheet (dialog) of rules specific to each type of defect and its location in the same. These rules may be used to determine which defects should be removed and a solution may be determined for the best face (top or bottom), and best edge (left or right). The solution may be displayed on a viewing screen while simultaneously transmitting the solution to the next machine process. The sample may transfer under the pinch roll assembly 62 which may slowly lower to provide continued conveyance onto the metal slide of the tail conveyor 58. As the trailing end of the sample leaves the pinch roll 63, the roll 63 may quickly lift as the stop brake 64 quickly lowers on to the surface of the sample and quickly lifts after arresting the sample's movement. The drop gate 61 may open (61*b*) allowing gravity to slide the sample off and out of the tail conveyor 58 completing the scanning process.

The foregoing description and drawings comprise illustrative embodiments. Having thus described exemplary embodiments, it should be noted by those skilled in the art that the within disclosures are exemplary only, and that various other alternatives, adaptations, and modifications may be made within the scope of the present disclosure. Merely listing or numbering the steps of a method in a certain order does not constitute any limitation on the order of the steps of that method. Many modifications and other embodiments will come to mind to one skilled in the art to which this disclosure pertains having the benefit of the teachings presented in the foregoing descriptions and the associated drawings. Although specific terms may be employed herein, they are used in a generic and descriptive sense only and not for purposes of limitation. Accordingly, the present disclosure is not limited to the specific embodiments illustrated herein, but is limited only by the following claims.

What is claimed is:

1. A scanning system to analyze wood and determine defects, the scanning system comprising:
    at least two ultrasonic transducers configured to scan the wood from edge to edge by triangulating the wood, wherein said at least two ultrasonic transducers are configured to find splits and shakes, wherein said at least two ultrasonic transducers are configured to determine a best edge and/or to confirm a hole by making sure of a true open area, wherein said at least two ultrasonic transducers comprise at least one pulsar and a corresponding at least one receiver, each said pulsar and the corresponding receiver being oriented at a same angle relative to a side of the wood, wherein each said pulsar injects sound into the wood on one side while the corresponding receiver on the other side of the wood records all escaping sound;
    a floating head attached to a supporting member configured to move freely in a perpendicular direction to the wood, said floating head having an angled front at a front end of the floating head configured for contacting the wood allowing the wood to move the floating head up and down;
    said at least two ultrasonic transducers being affixed to the floating head at a position configured to maintain an air gap between a top edge of the wood and the at least two ultrasonic transducers;
    wherein, when the wood is moved under the floating head, said floating head moves freely up and down, whereby said at least two ultrasonic transducers maintaining the air gap between said ultrasonic transducers and the wood.

2. The scanning system according to claim 1, wherein said at least two ultrasonic transducers are set to a frequency.

3. The scanning system according to claim 2 wherein said frequency is:
    between 60-80 khz.

4. The scanning system according to claim 1 wherein said angle is:
    between 5 degrees and 20 degrees.

5. The scanning system according to claim 4 wherein each said receiver are offset in a direction of said angle a distance equal to a width of the transducers, wherein an offset alignment of the receiver allows a sonic cone of each transducer to align parallel with its adjacent pair of said pulsar and the corresponding receiver.

6. The scanning system according to claim 1 wherein said air gap is:
    between 0.10 inches and 1.00 inch.

7. The scanning system according to claim 1 further including at least one camera for visual defects that is configured for imaging top and bottom surface of the wood, wherein said at least two ultrasonic transducers and said at least one camera combine to analyze the wood.

8. The scanning system according to claim 7 wherein said at least one camera includes a monochrome camera, a true color area scan camera, a 3D profiling camera, or combinations thereof.

9. The scanning system according to claim 8 wherein said at least one camera including structured lighting including:
   invisible infrared lighting for the monochrome camera configured to image rough sawn wood samples, reduce the contrast of color variance, and/or aid in the analysis of defects for rough side processing;
   natural white lighting for the true color area scan camera configured to enhance contrast, and/or to aid in the analysis of defects and wood grade for surfaced/milled wood samples;
   invisible or visible lasers with line generators for the 3D profiling camera configured to strike a surface of a sample at 45° being offset respective of the surface's irregularity; or
   combinations thereof.

10. The scanning system according to claim 7 wherein said at least one camera is configured to contrast the wood.

11. The scanning system according to claim 1 further including a feed conveyor with a cradle configured to bring the wood in on two sides allowing the wood to bow naturally.

12. The scanning system according to claim 1 further comprising:
   a feed conveyor;
   a scan box;
   a tail conveyor; and/or
      a computer device configured to control the feed conveyor, the scan box, the tail conveyor, or combinations thereof.

13. The scanning system according to claim 12, wherein the computer device is configured to have two different setups, a first setup for rough wood, and a second setup for surfaced wood.

* * * * *